(12) United States Patent
Rosmarin et al.

(10) Patent No.: US 9,085,413 B2
(45) Date of Patent: Jul. 21, 2015

(54) METHODS AND SYSTEMS ADAPTED TO HANDLE STICKY SAMPLE CONTAINERS

(75) Inventors: Matthew Anthony Rosmarin, Flushing, NY (US); Vadim Filler, Bronx, NY (US); Neil Simon Thomas, Rivervale, NJ (US); Adam Justin Perlman, Ridgewood, NJ (US); Thomas Creazzo, Tuxedo, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 13/814,423

(22) PCT Filed: Aug. 4, 2011

(86) PCT No.: PCT/US2011/046563
§ 371 (c)(1),
(2), (4) Date: Feb. 5, 2013

(87) PCT Pub. No.: WO2012/018993
PCT Pub. Date: Feb. 9, 2012

(65) Prior Publication Data
US 2013/0136569 A1 May 30, 2013

Related U.S. Application Data

(60) Provisional application No. 61/371,196, filed on Aug. 6, 2010.

(51) Int. Cl.
*B65H 31/30* (2006.01)
*B65B 5/10* (2006.01)
*B65G 1/04* (2006.01)
*G01N 35/00* (2006.01)
*B25J 9/16* (2006.01)
*B65B 5/08* (2006.01)

(52) U.S. Cl.
CPC ............... *B65G 1/04* (2013.01); *B25J 9/1612* (2013.01); *G01N 35/0099* (2013.01); *B65B 5/08* (2013.01)

(58) Field of Classification Search
CPC ............. B66F 9/18; B25J 9/041; B23Q 7/04; B65B 5/08; B65B 5/105; B65B 5/106; B65B 35/16
USPC .......... 414/618, 790.2, 790.3; 422/63, 65, 67, 422/68.1, 72; 53/473, 475, 244, 246
See application file for complete search history.

(56) References Cited

U.S. PATENT DOCUMENTS

| 4,522,089 | A  | * | 6/1985  | Alvi .......................... 81/3.42 |
| 6,544,799 | B1 | * | 4/2003  | Lewis et al. ................ 436/180 |
| 6,586,255 | B1 | * | 7/2003  | Hubert et al. ................. 436/45 |
| 2003/0135984 | A1 | * | 7/2003  | Nayar et al. .............. 29/603.03 |
| 2007/0059209 | A1 | * | 3/2007  | Pang et al. .................... 422/72 |
| 2009/0260208 | A1 | * | 10/2009 | Takeuchi et al. .............. 29/282 |
| 2010/0104404 | A1 | * | 4/2010  | Yokoo et al. ............. 414/226.01 |

FOREIGN PATENT DOCUMENTS

| IT | WO2008107769 A2 * | 9/2008 | ............. B25J 9/16 |
| JP | H0311530 U | 2/1991 | |
| JP | Hei 09-010605 A | 1/1997 | |
| JP | 2000-317871 A | 11/2000 | |
| JP | 2002-533200 A | 10/2002 | |
| JP | 2003-080487 A | 3/2003 | |
| JP | 2006-177961 A | 7/2006 | |
| JP | 2010-505128 A | 2/2010 | |

* cited by examiner

*Primary Examiner* — Saul Rodriguez
*Assistant Examiner* — Emery Hassan
(74) *Attorney, Agent, or Firm* — Dugan & Dugan, PC

(57) ABSTRACT

Disclosed are methods and systems adapted to aid in a handling of sample containers (e.g., sample containers) in a processing or testing system. The method includes a sequence of motions of gripper fingers and a seater to accomplish a pick and place operation of a sample container where the sample container includes a sticky surface. A sample container positioning system is disclosed, as are other aspects.

12 Claims, 9 Drawing Sheets

METHODS AND SYSTEMS ADAPTED TO HANDLE STICKY SAMPLE CONTAINERS

RELATED APPLICATIONS

The present application claims priority to U.S. Provisional Patent Application Ser. No. 61/371,196, filed Aug. 6, 2010, and entitled "APPARATUS AND METHOD FOR THE INTELLIGENT HANDLING OF STICKY SAMPLE CONTAINERS," which is hereby incorporated herein by reference in its entirety for all purposes.

FIELD OF THE INVENTION

The present invention relates generally to methods and systems adapted to handle sample containers.

BACKGROUND OF THE INVENTION

In medical testing and processing, the use of robotics may minimize exposure to, or contact with, biological fluid samples (otherwise referred to as "specimens") and/or may increase productivity. For example, in some automated testing and processing systems (e.g., clinical analyzers), sample containers, such as sample containers, sample cups, vials, small sample cups (SSCs), and the like, may be transported to and from testing and/or processing systems by an automated transport system. The sample containers may be presented in the system at a staging or pickup area where information is read from the sample container (e.g., from a bar code), and thereafter the sample containers may progress into the system for processing and/or testing.

Such transportation of the sample container may be accomplished by the use of an automated mechanism such as a robot including two or more gripper fingers adapted to grasp the sample container (e.g., sample container) on the sides thereof. The sample container may then be moved from one location to another (e.g., to a destination receptacle) in relationship to the testing or processing system. However, in some instances, the sample container may be improperly positioned relative to the destination receptacle or the gripper fingers. Accordingly, methods and systems that may improve accuracy of positioning of a sample container within a testing and/or processing system are desired.

SUMMARY OF THE INVENTION

In a method aspect, an improved method of positioning a sample container is provided. The method includes gripping the sample container with gripper fingers of a gripper assembly; descending the gripper assembly and sample container to partially insert the sample container into a destination receptacle; ungripping the gripper fingers from the sample container; while ungripped, pushing the sample container into the destination receptacle with a seater; re-gripping the sample container with the gripper fingers; retracting the seater; again ungripping the gripper fingers from the sample container; and further descending the gripper fingers.

According to another aspect, a sample container positioning system is provided. The sample container positioning system includes a robot including a moveable robot component; a gripper assembly mounted to the moveable robot component, the gripper assembly including gripper fingers adapted to grip a sample container; and a controller operable to cause: gripping of the sample container with the gripper fingers of the gripper assembly, descending of the gripper assembly and sample container to partially insert the sample container into a destination receptacle, ungripping of the gripper fingers from the sample container, while ungripped, pushing the sample container into the destination receptacle with a seater, re-gripping of the sample container with the gripper fingers, retracting of the seater, again ungripping the gripper fingers from the sample container, and further descending the gripper fingers.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the spirit and scope of the present invention. Accordingly, the drawings and descriptions are to be regarded as illustrative in nature, and not as restrictive. The drawings are not necessarily drawn to scale. The invention is to cover all modifications, equivalents, and alternatives falling within the spirit and scope of the invention.

DETAILED DESCRIPTION

Figure 1A:
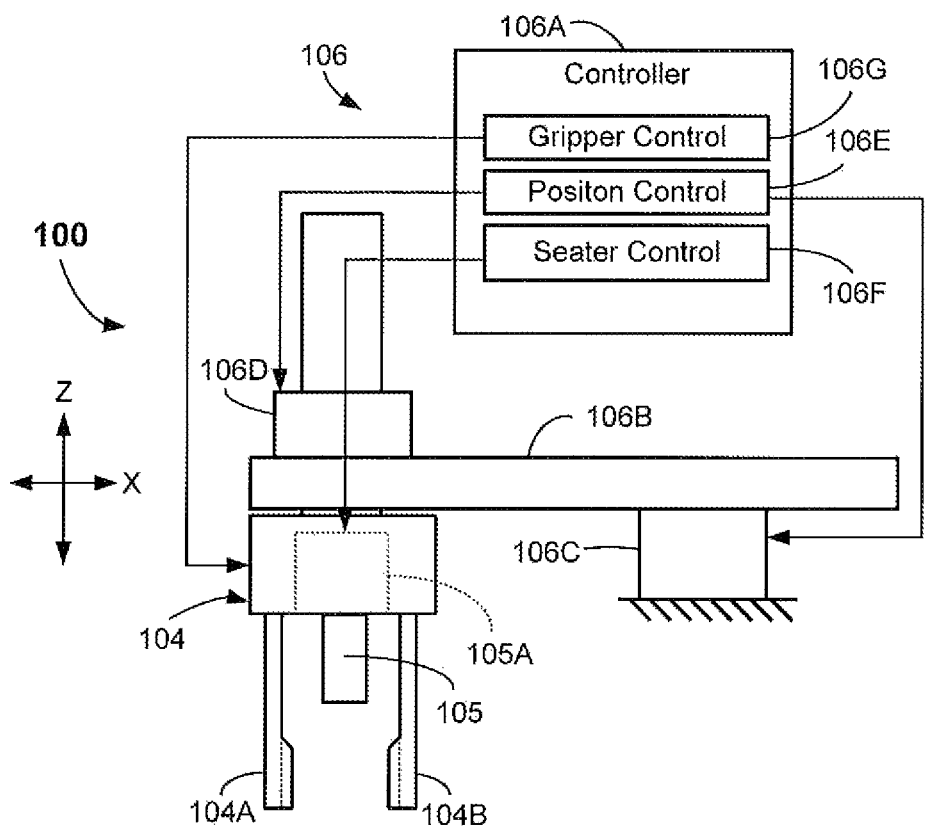
FIG. 1A is a side view illustration of an example robotic system shown ready to pick up a sample container (e.g., sample container) that is provided at a pickup location according to embodiments of the invention.
Figure 1A:
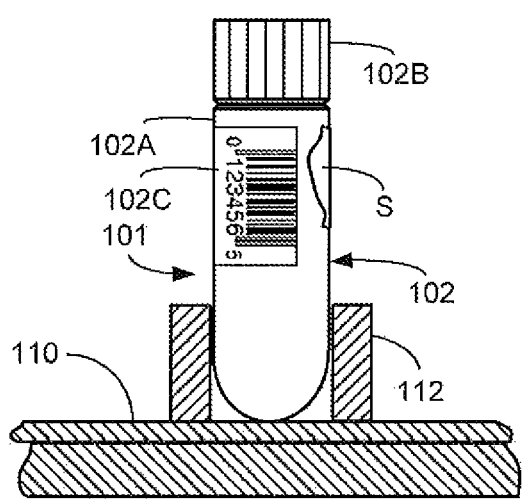

In some instances, sample containers may have sticky surfaces on them due to spilled contaminants, adhesive label residue, curled labels exposing label adhesive, or soft caps having inherent stickiness due to the nature of the material used or slight deformation of the soft cap by the gripper fingers. In the following example, a sample tube is described. However, it should be understood that the present invention may be used to handle any type of sample container having one or more sticky surfaces thereon. Sticky surfaces may be on the sample tube body or cap. As used herein, the term "sample container" may refer to either a capless sample container or a capped sample container. Sample container is any vessel adapted to receive a material (e.g., a biological fluid such as blood, blood serum, urine, interstitial fluid, or other bodily fluid) for processing and/or testing. Examples of sample containers are blood collection containers, urine collection containers, and the like. Such sticky surfaces may cause problems in the positioning of the sample container, in that the sample container may adhere to one or more of the gripper fingers of a gripper assembly that is used to transport the sample container from one location to another. Moreover, the one or more sticky surfaces may otherwise adhere to other system components, such as a container seater or sample rack. As such, placement of the sample container at a desired destination receptacle location may be improperly carried out. For example, the sample container may be positioned at a location other than a bottom of a container receptacle (e.g., a sample rack) due to adherence between the one or more sticky surfaces on the sample container and one or more of the gripper fingers. In other words, the sample container may be partly retracted from a preferred position in the sample rack (e.g., sit too high in the rack). In later process steps, this may result in a sample nozzle being positioned too close to the bottom of the sample container during sample aspiration. In other instances, the sample container may be pulled entirely back out of the container receptacle by the adherence to the sticky surface, and may fall, shatter, contaminate, or otherwise disrupt smooth operation of the processing or testing system. In other instances, adherence at the pickup location may cause the cap to be partially or entirely pulled off. Furthermore, improper positioning of the sample container in the gripper fingers may cause a crash risk with other components of the testing or processing system.

In view of the foregoing problems, in one aspect, a method of positioning a sample container (e.g., sample tube) that eliminates or minimizes the occurrences of improper positioning experienced by prior art methods is provided. Accordingly, samples containers may be precisely located at a predetermined height location in the gripper fingers and/or within a destination receptacle.

In a first aspect, a method of positioning the sample container is provided. The method utilizes a sequence of motions of a seater, gripper fingers, and one or more robotic components to eliminate or minimize instances of improper positioning when sticky surfaces are encountered on the sample container.

These and other aspects and features of the invention will be described with reference to FIGS. 1A-2 herein.

In accordance with a first embodiment of the invention, as best shown in FIGS. 1A through 1I, a sample container positioning system 100 is shown in various orientations. In one aspect, the sample container positioning system 100 is adapted to carry out the present method. The sample container positioning system 100 is useful for precisely transporting one or more sample containers 102 from a pickup location 101 to a destination receptacle 103A (FIGS. 1D-1I). The sample container 102 may be any size (e.g., small, medium, or tall), and in some embodiments may include a sample container body 102A and cap 102B, for example. The sample container positioning system 100 includes a gripper assembly 104 including two or more moveable fingers, such as opposed, relatively-moveable fingers 104A, 104B, and a seater 105.

The moveable fingers 104A, 104B may be laterally retractable and adapted to grip the sample container body 102A and/or cap 102B on the sides thereof. More than two fingers may be provided (e.g., three or four). The seater 105 may be axially moveable and may be moved into contact with a top (e.g., a cap 102B) of the sample container 102 and then retracted therefrom. Any suitable mechanism 105A for extending and retracting the seater 105 may be used, such as a linear motor.

In some embodiments, vertical and/or horizontal motions of the gripper assembly 104 in space may be controlled by a robot system 106. The robot system 106 may include a controller 106A, one or more robot components 106B, such as one or more robot arms, and one or more drive motors 106C, 106D. The robot system 106 may be provided in any suitable orientation relative to the sample container 102, such that the sample container 102 may be picked up at a pickup location 101 and transferred to another location (e.g., to a destination receptacle 103A of a sample rack 103, FIGS. 1D-1I) for further processing and/or testing.

As shown in FIG. 1A, the gripper assembly 104 is moveable in at least the X and Z directions, for example. The robot system 106 may include other degrees of freedom (e.g., X, Y (extending into and out of each drawing sheet of FIGS. 1A, 1B, and 1D-1I), and Z) or even rotation about an X, Y, and/or Z axes. The controller 106A may command the drive motor 106C and robot component 106B to move the gripper assembly 104 in one or more coordinate directions, or two or more coordinate directions, or three or more coordinate directions. Any suitable robot system 106 including one or more moveable robot components 106B may be used, such as a moveable robot arm, moveable boom, or moveable beam having the gripper assembly 104 mounted and mechanically coupled thereto. In some embodiments, the moveable component of the robot system 106 may include one or more shoulder, elbow, or wrist elements to accomplish two-dimensional or three-dimensional motion of the gripper assembly 104. In some embodiments, the gripper assembly 104 may be moveable in the +X or −X direction by drive motor 106C, and may be moveable along one or more additional tracks, slides, or guides in an additional direction (e.g., the Y direction). Optionally, the drive motor 106C may be a rotational motor rotating the moveable component 106B (e.g., robot arm) in an X-Y plane. Vertical motion of the gripper assembly 104 in the +Z or −Z direction relative to the moveable robot component 106B (e.g., robot arm) may be accomplished by a vertical drive motor 106D.

In other embodiments, the robot system 106 may include a frame and a moveable gantry arrangement with the gripper assembly 104 being mounted to a boom or beam thereof. The boom or beam may be moveable (e.g., in the X direction) on a suitable track, slide, worm drive, or guide mechanism by suitable drive motor 106C. Furthermore, the boom (and the gripper assembly 104) may be moveable along one or more additional tracks, slides, or guides in an additional direction (e.g., the Y direction). Vertical motion of the gripper assembly 104 in the Z direction relative to the boom or beam may be accomplished by a vertical drive motor 106D. The means for moving the robot system 106 in the various coordinate directions may include any suitable number of conventional motion-producing mechanisms, such as one or more electrical motors, stepper motors, servo motors, pneumatic or hydraulic motors, etc. Furthermore, drive systems adapted to couple to the drive motors 106C, 106D may include chains and sprockets, guides, pulleys and belt arrangements, drives such as gear drives or worm drives, or other conventional drive components, and may be utilized to cause the motion of the robot system 106 and coupled gripper assembly 104. Other suitable types of robot systems upon which the gripper assembly may be mounted may be employed.

The sample container positioning system 100 depicted may be part of a biological fluid testing system, such as a clinical chemical analyzer. The sample container positioning system 100 may move a sample container to a destination location where the sample container may be decapped so that a portion of a sample biological fluid contained in the sample container may be aspirated and tested. In other embodiments, the sample container positioning system 100 may be used to transport the sample container containing sample fluid to another location for further processing (e.g., centrifuging).

Again referring to FIG. 1A, as part of the method, the gripper assembly 104 may be aligned horizontally in the X direction and Y direction by drive motor 106C with the sample container 102 so that the gripper assembly 104 is positioned vertically above the sample container 102. The sample container 102 may be driven along the X direction by a transportation lane 110 that may cause the positioning of the sample container 102 in the X direction. A pickup receptacle, sample carrier, or puck 112 may hold the sample container 102 and carry the sample container 102 to a desired pickup location 101 for pickup by the gripper assembly 104. At this stage, the sample container 102 is presented to the robot system 106 for pickup. At or near the pickup location 101, a barcode 102C on the sample container body 102B may be read and verified and communicated to the controller 106A, which may then determine the destination for one or more tests and/or processing to take place on the sample container 102.

The controller 106A may include a position control 106E, such as an algorithm adapted to control a vertical and lateral position of the gripper assembly 104 relative to the pickup location 101 and a delivery destination (e.g., a destination receptacle 103A, FIGS. 1D-1I), and a seater control 106F to command the execution of extending and retracting motions of the seater 105 at various times during the method. Suitable feedback mechanism(s) or sensor(s) may be provided such that feedback information of a position of the robot arm 106B and gripper assembly 104 and in coordinate space is provided. Suitable feedback mechanism(s) or sensor(s) may be provided such that feedback information of a position of the seater 105 may be provided. Height sensing may also be provided. The height sensing may be configured and adapted to indicate a height of any object that the seater 105 comes into contact with (e.g., a cap 102B). For example, in some embodiments, the height sensing may comprise a suitable electrical circuit coupled to a linear motor driving the seater 105, wherein a load may be applied to the cap 102B by the seater 105 and a displacement of the seater 105 relative to the gripper assembly 104 may be monitored in the Z direction. Accordingly, a Z position of the seater 105 may be determined and stored in memory of the controller and used to carry out the method. Gripper control 106G is adapted to control the gripping and ungripping of the gripper fingers 104A, 104B at various points in the method.

Figures 1B, 1C:
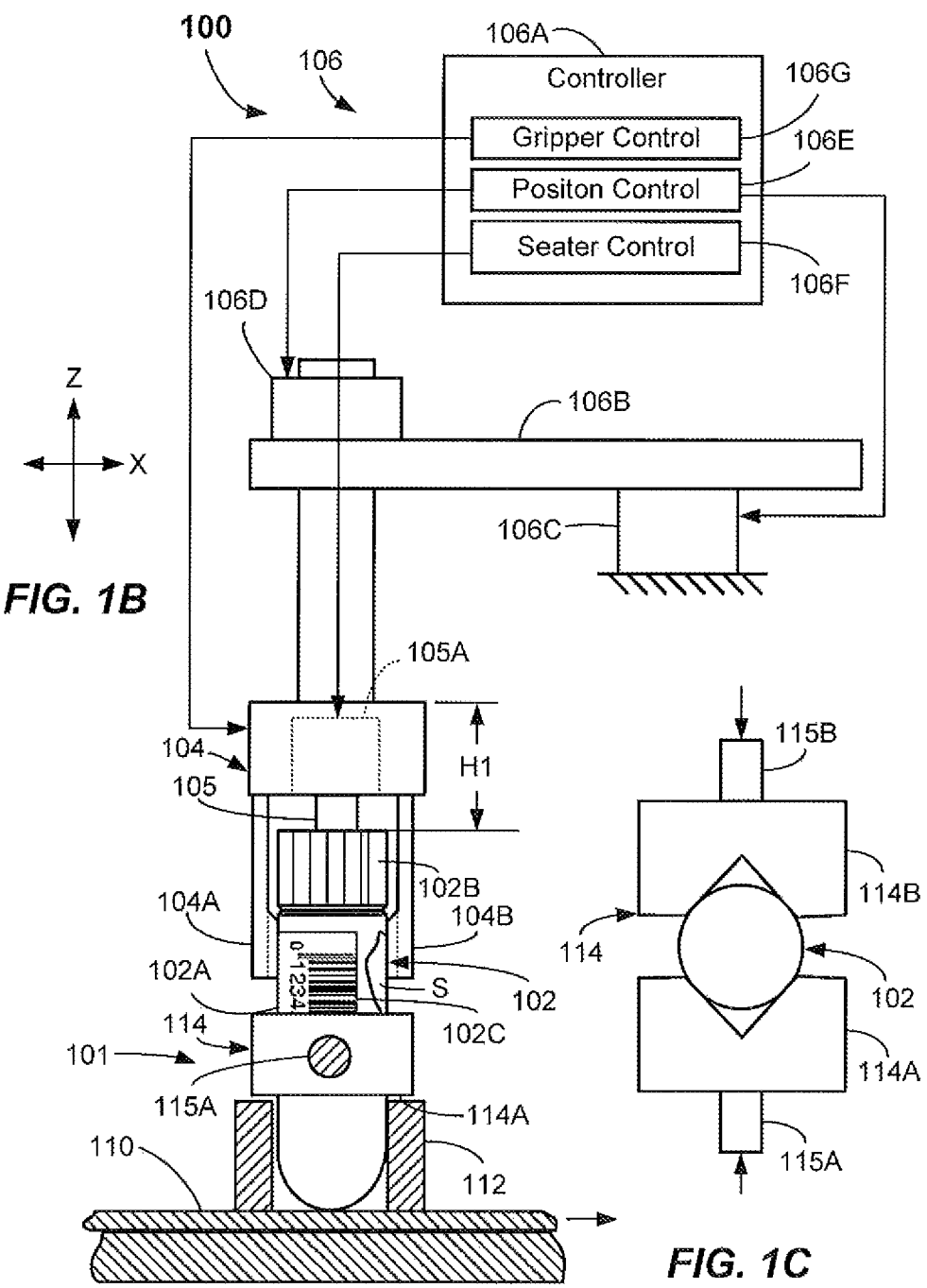
FIG. 1B is a side view illustration of an example robotic system picking up a sample container provided at a pickup location according to embodiments of the invention.
FIG. 1C is a top view of an example straightening device holding a sample container at a pickup location according to embodiments of the invention.
Figure 2:
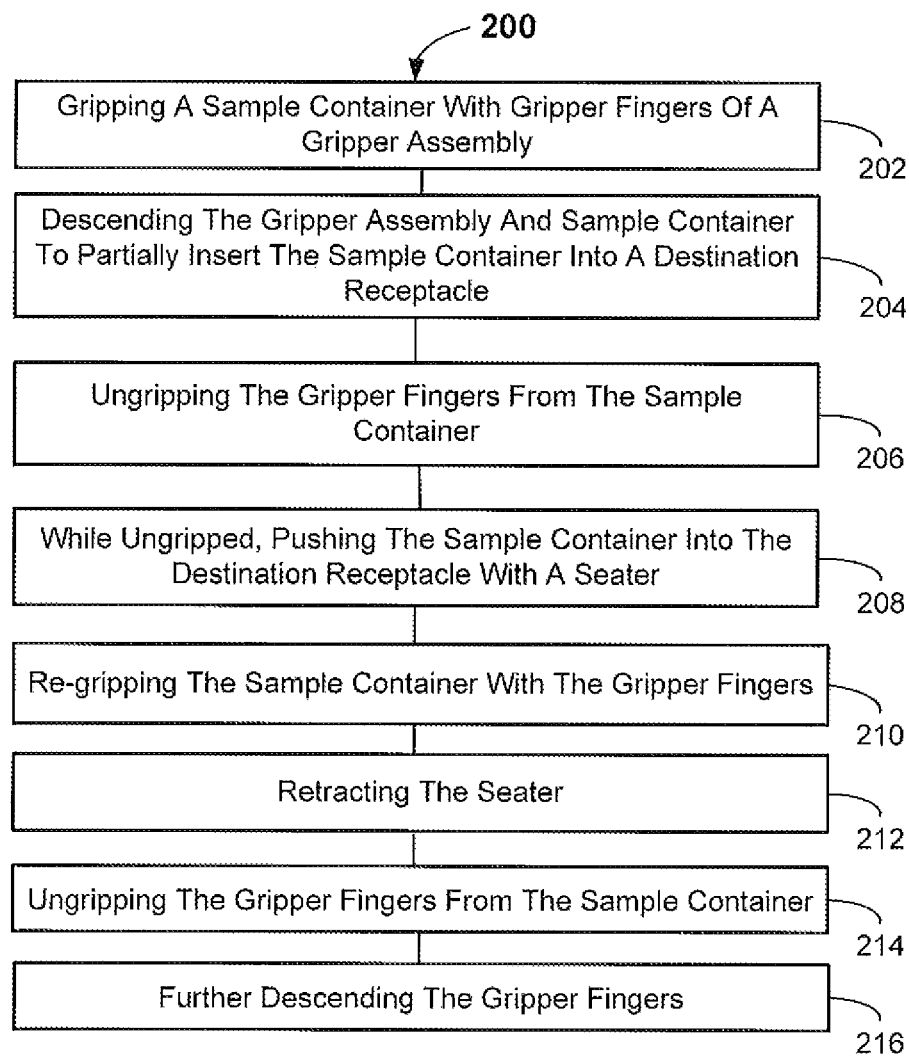
FIG. 2 is a flowchart illustrating a method according to embodiments of the present invention.

In more detail, the sample container positioning system 100, as shown in FIG. 1B, may include a container straightening device 114 adapted to close on and contact the container body 102A laterally when the sample container 102 is appropriately positioned at the pickup location 101. The transportation lane 110 may stop for pickup at the pickup location 101 or the puck 112 and container straightening device 114 may both move along together and the sample container 102 may be picked up at the pickup location 101 while the sample container 102 is still moving in the X direction. The container straightening device 114 may include, as is shown in FIG. 1C, halves 114A, 114B that are caused by actuators 115A, 115B (only a portion shown) to close on and contact the container body 102A of sample container 102 and cause the sample container 102 to be grappled and positioned in an upright orientation or pickup. Once the container straightening device 114 has successfully oriented the sample container 102, the robot system 106 may descend and encapsulate and grasp the sides of the sample container 102 as is shown in FIG. 1B. Thus, at this point in the method, the fingers 104A, 104B are coupled to the sample container 102. The robot system 106 may wait a fixed period of time to ensure a suitable grip is achieved.

After the fixed period of time (e.g., a few seconds), the container straightening device 114 will open the halves 114A, 114B and decouple from the sample container 102. A sensor at the container straightening device 114 may determine that the sample container 102 is separated from the container straightening device 114. Now the seater control 106F will cause the seater 105 to extend and descend downwardly (in the Z direction) to come into contact with the cap 102B of the sample container 102 with a light amount of force (e.g., about less than one lbf.). When the seater 105 contacts the cap 102B at the top of the sample container 102, the seater control 106F registers a height (H1) of the top of the sample container 102 (e.g., the cap 102B) relative to a fixed point on the gripper assembly 104. If H1 is below a threshold value HT, i.e., H1<HT, then an error may be flagged because the sample container 102 may be cracked or may be missing a cap 102B. If an error is flagged, then the system 100 may be stopped for corrective action.

If no error is noted, then the gripper assembly 104 and sample container 102 may be lifted from the pickup location 101 to a predetermined lateral transport height in the Z direction as dictated by the position control 106E. At this lateral transport height, the seater 105 may again measure (via seater control 106F) a position H2 in the Z direction of the top of the sample container 102 (e.g., the cap 102B) relative to a fixed point on the gripper assembly 104. If H2 is the same as H1, then the sample container 102 is still properly positioned and grasped by the gripper fingers 104A, 104B. If H2>H1, then the sample container 102 may have slipped in the gripper assembly 104 and an error may be flagged. If an error is flagged, then corrective action may be taken, such as stopping, indicating an error, or sounding an audible alarm.

If no error is flagged, the robot system 106 may move the gripper assembly 104 through a predetermined transportation path (e.g., laterally) to a final destination. The final destination may be a position above a destination receptacle 103A in a sample rack 103 (FIGS. 1D-1I), for example. Once in position, a placing operation may commence.

Figure 1D:
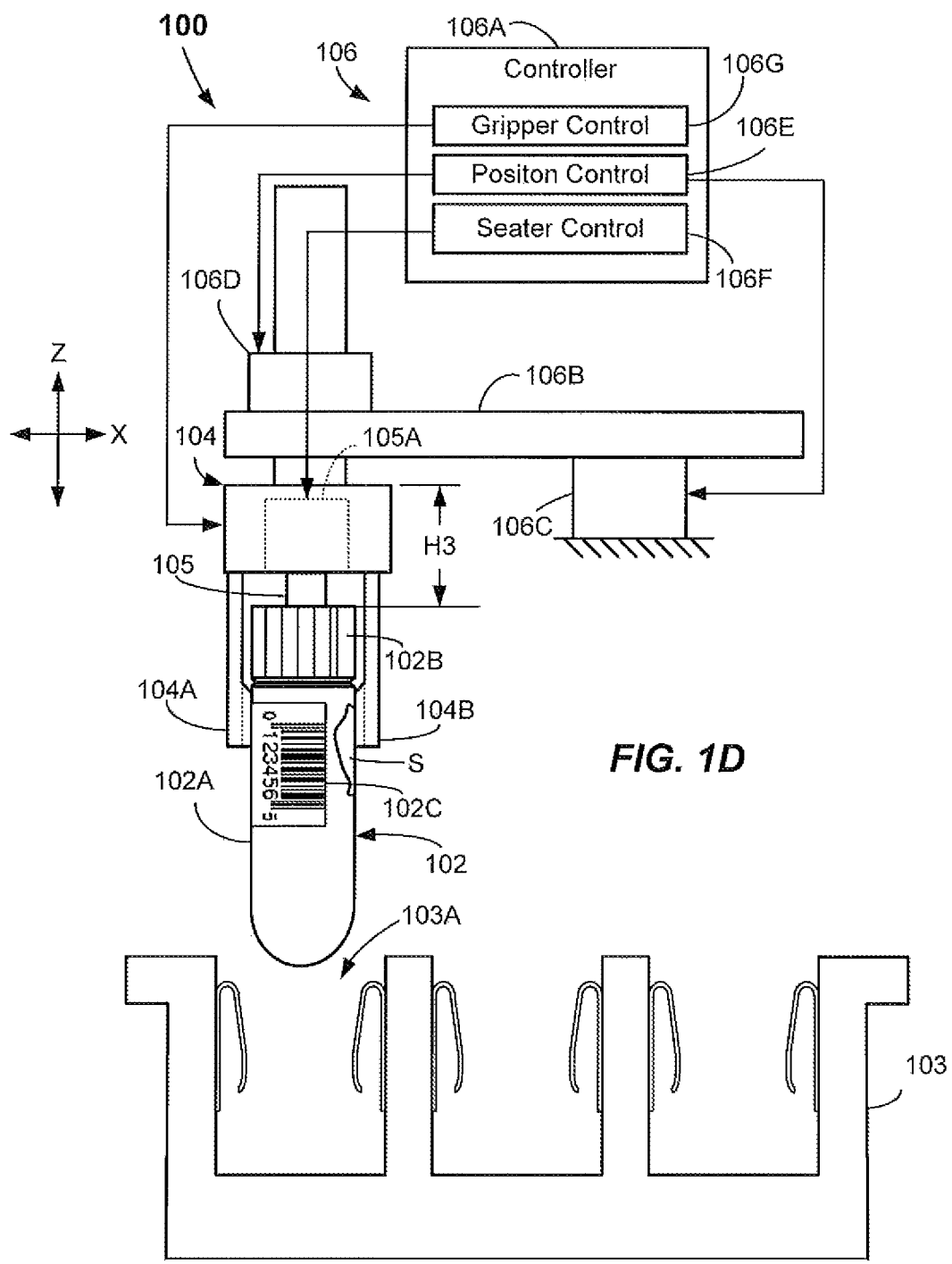
FIG. 1D is a side view of an example robotic system holding a sample container for insertion into a destination receptacle at a delivery destination according to embodiments of the invention.
Figure 1E:
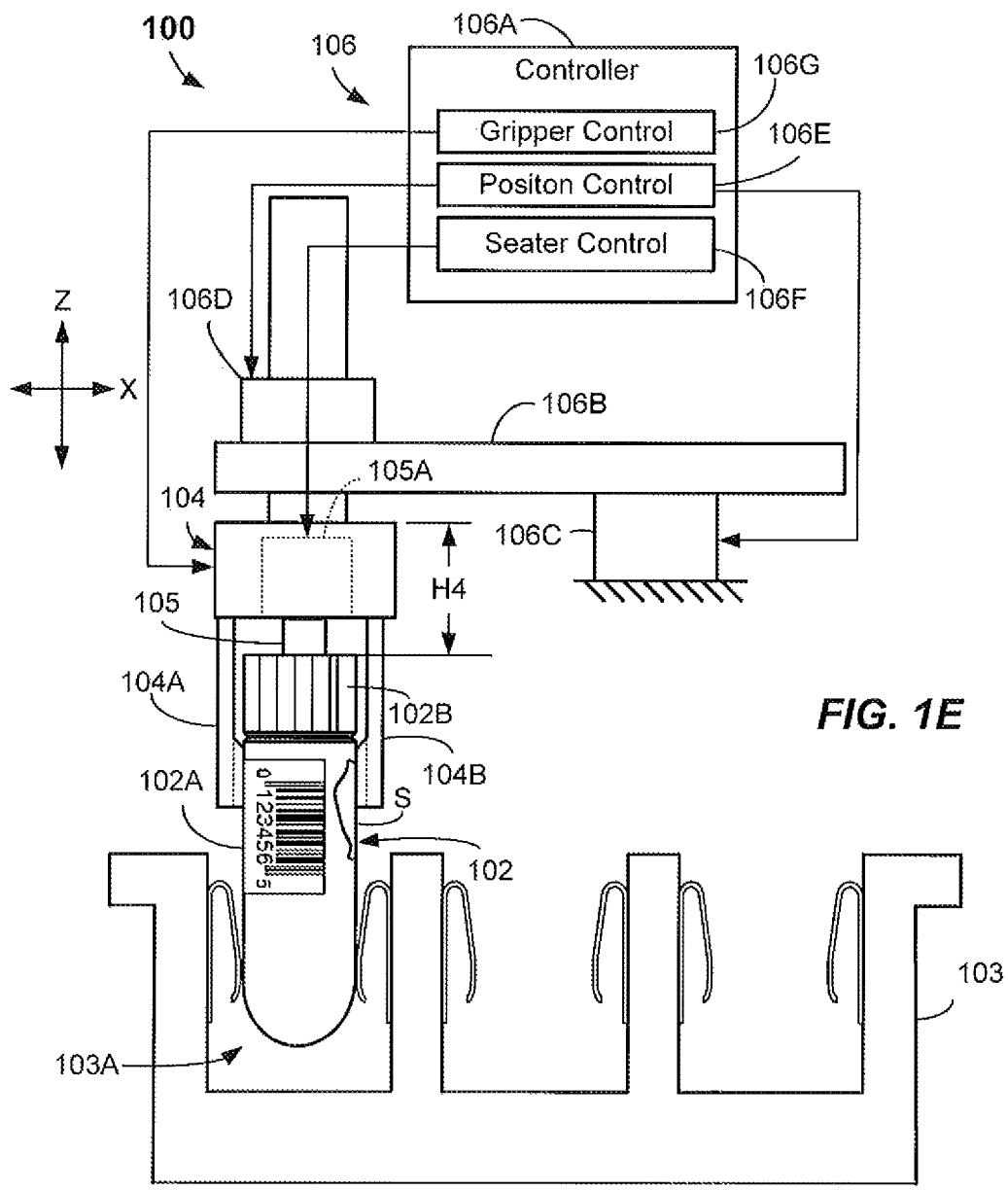
FIG. 1E is a side view of an example robotic system partially inserting a sample container (e.g., sample tube) into a destination receptacle at a delivery destination according to embodiments of the invention.

As shown in FIG. 1D, the sample container 102 is positioned over the destination receptacle 103A at a predetermined height location. The destination receptacle 103A may be a receptacle of a sample rack 103, for example. Otherwise, the destination receptacle 103A may be any location in the testing or processing system. Once there, the seater 105 may again be extended with a small force and engaged with the top of the sample container 102 (e.g., the cap 102B) to measure a height H3 of the sample container 102 relative to a fixed point on the gripper assembly 104 and determine if any slippage has occurred as compared to H2. If, after applying a small force, no displacement change is noted, then no slippage has occurred. The seater 105 may then be locked in place in contact with the top of the sample container 102 (e.g., the cap 102B) by any suitable locking means. Locking may be accomplished by a mechanical locking mechanism or, in the case of a linear motor being used to extend and retract the seater 105, a closed loop position feedback may be used to keep the seater 105 positioned at height H3 regardless of the applied force. The gripper assembly 104 is then commanded by position control 106E to descend the sample container 102 and partially insert the sample container body 102A into the destination receptacle 103A as shown in FIG. 1E.

When the sample container body 102A is positioned at the desired height in the destination receptacle 103A, the seater 105 again measures (via seater control 106F) a height H4. This height is compared to the previously-measured height H3 and, if the difference is greater than a predetermined threshold, then an error may be flagged indicating the sample container 102 may have slipped during insertion into the receptacle 103A. The aforementioned height value H3 and H4 may be recorded in memory.

Figure 1F:
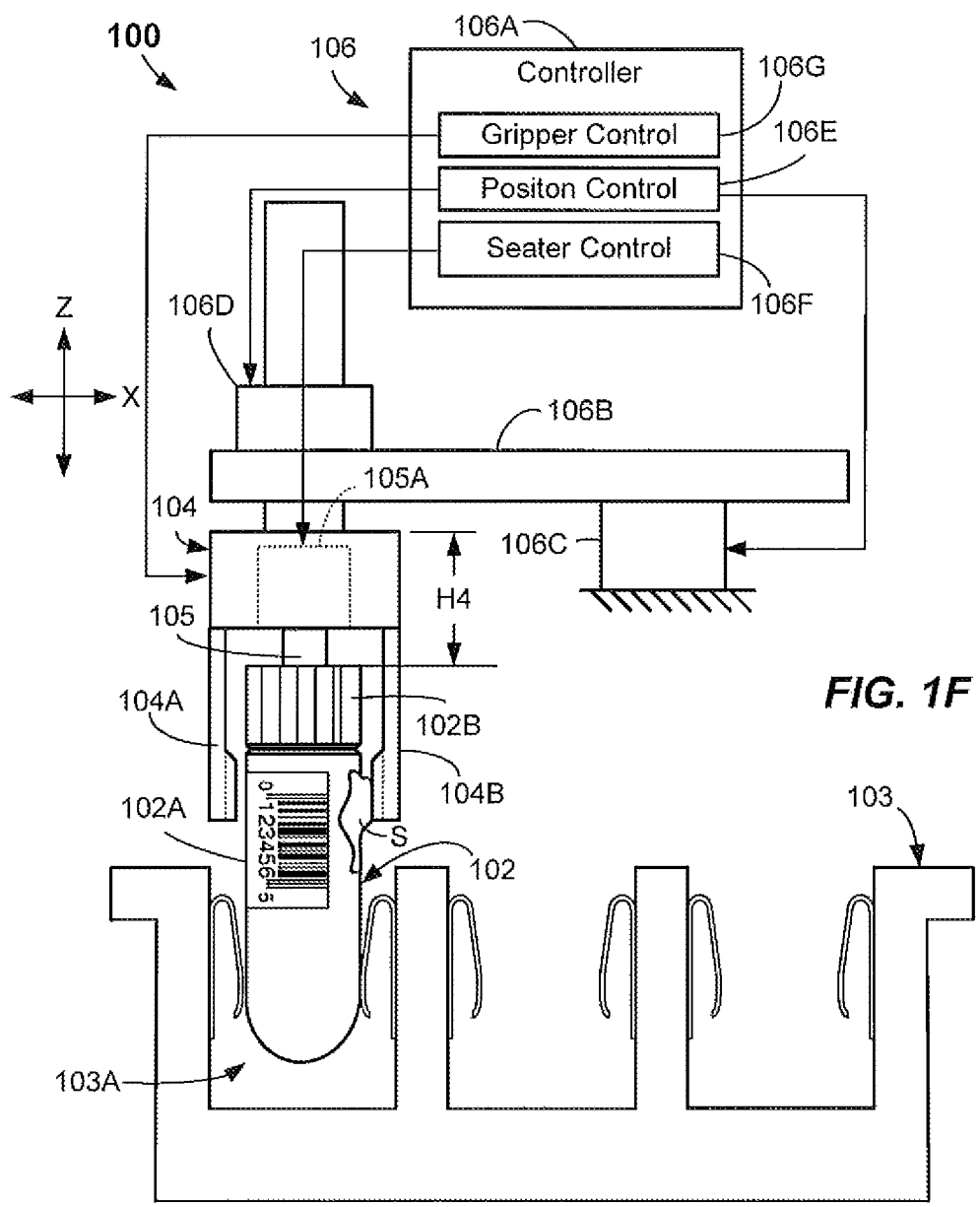
FIG. 1F is a side view of an example robotic system decoupling gripper fingers from a sample container prior to full insertion into the destination receptacle at a delivery destination according to embodiments of the invention.
Figure 1G:
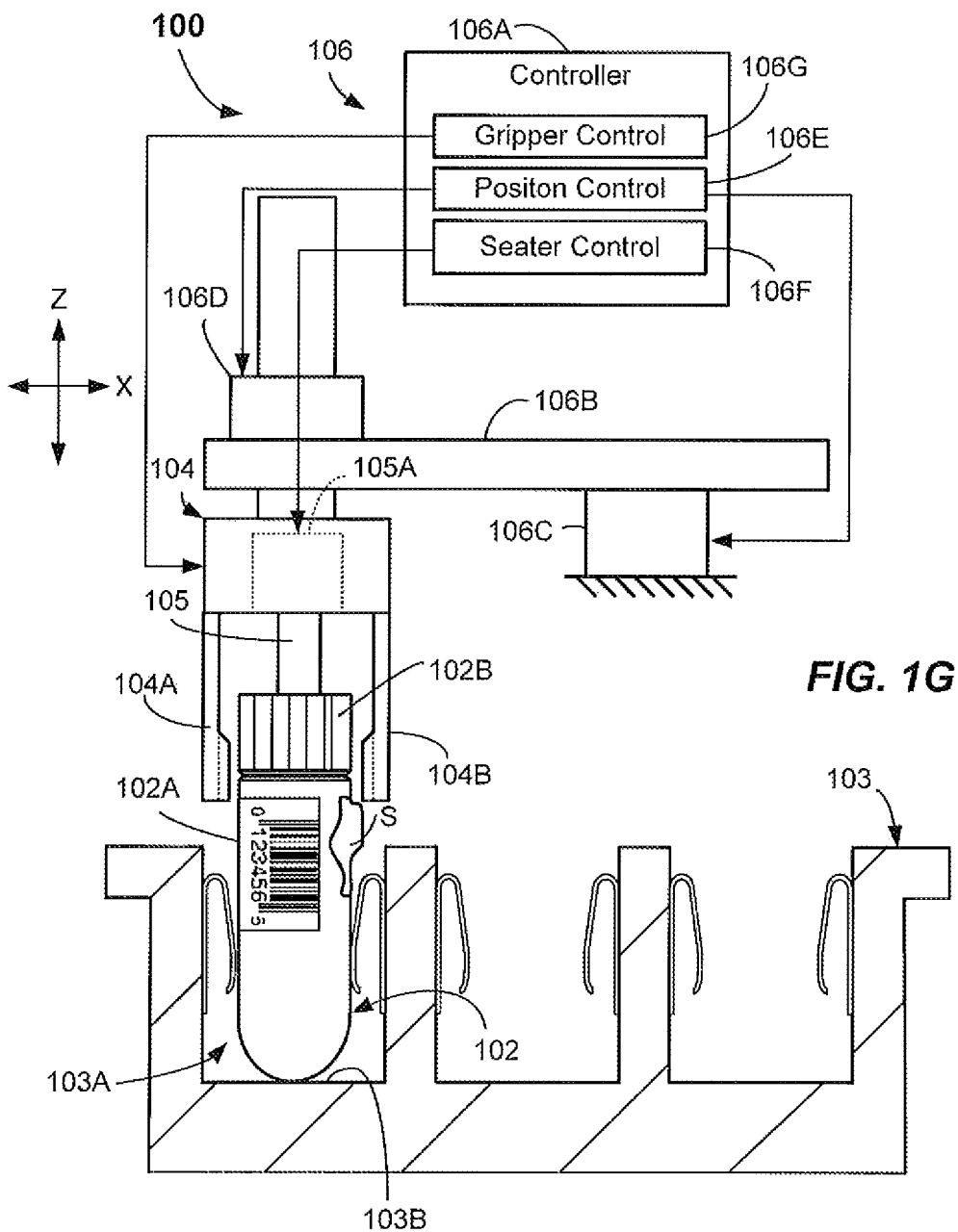
FIG. 1G is a side view of an example robotic system fully inserted (e.g., bottoming out) a sample container in the destination receptacle at a delivery destination by a seater according to embodiments of the invention.

If no error is noted, then the gripper fingers 104A, 104B will be opened to decouple the gripper fingers 104A, 104B from the sample container body 102A as is shown in FIG. 1F. At this point, with the sample container 102 being ungripped, the seater control 106F of the controller 106A will provide a control signal to the seater 105 and cause the seater 105 to extend and further insert the sample container 102 into the destination receptacle 103A. In some embodiments, the seater 105 will continue to push the sample container 102 until the bottom of the sample container 102 comes into contact with the bottom surface of the destination receptacle 103A, i.e., the sample container 102 is bottomed out in the destination receptacle 103A as shown in FIG. 1G. For example, as the seater 105 exerts a force on the cap 102B of the sample container 102, the bottom of the body 102A of the sample container 102 will contact the bottom 103B of the destination receptacle 103A. Any suitable feedback sensing may be provided in an electronic circuit for the drive motor 105A for the seater 105. The feedback may be used to determine bottoming. For example, a closed loop displacement feedback or force feedback may be used with the drive motor 105A.

Figure 1H:
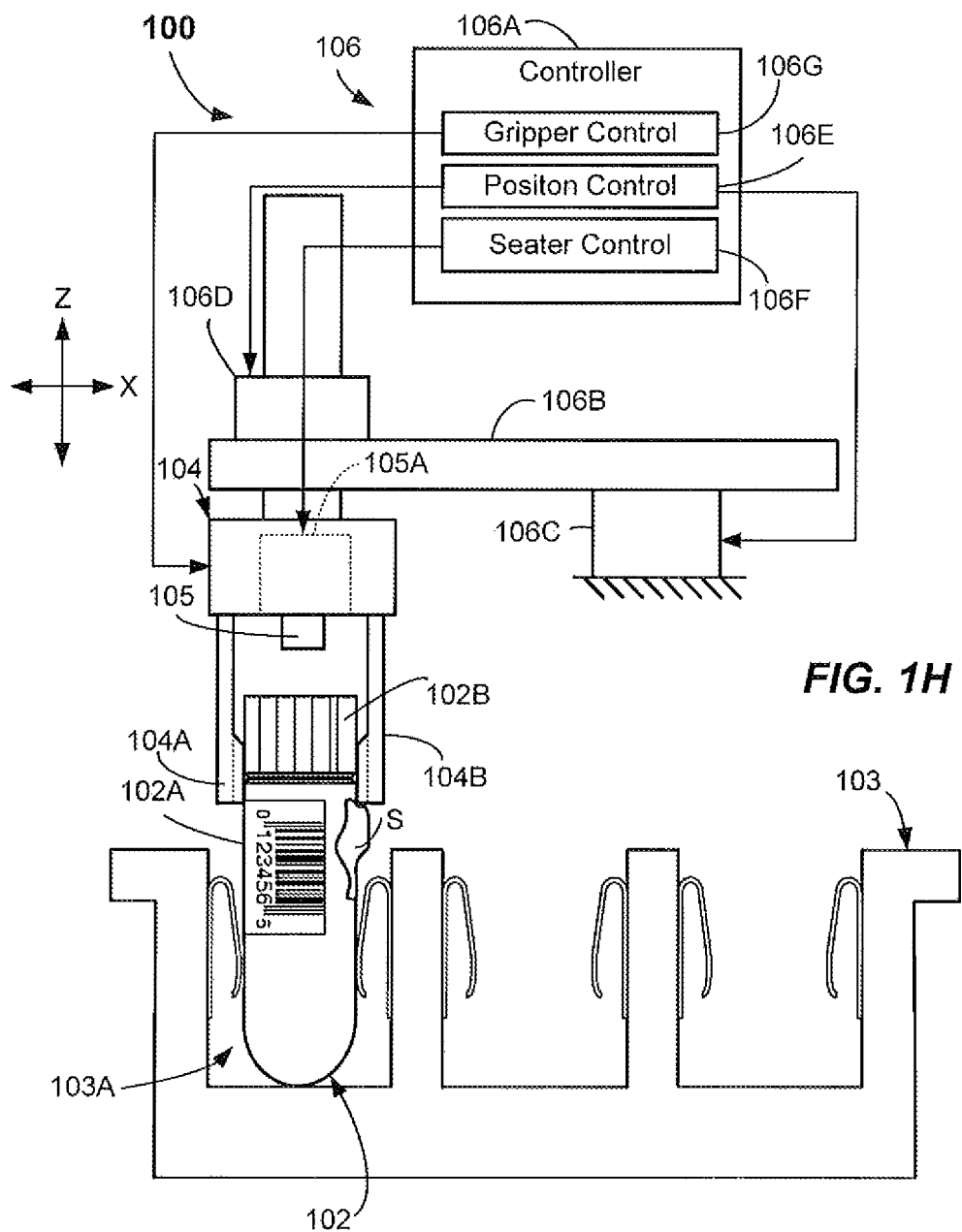
FIG. 1H is a side view of an example robotic system again coupling the gripper fingers to the sample container after full insertion into the destination receptacle at a delivery destination and then retracting the seater according to embodiments of the invention.
Figure 1I:
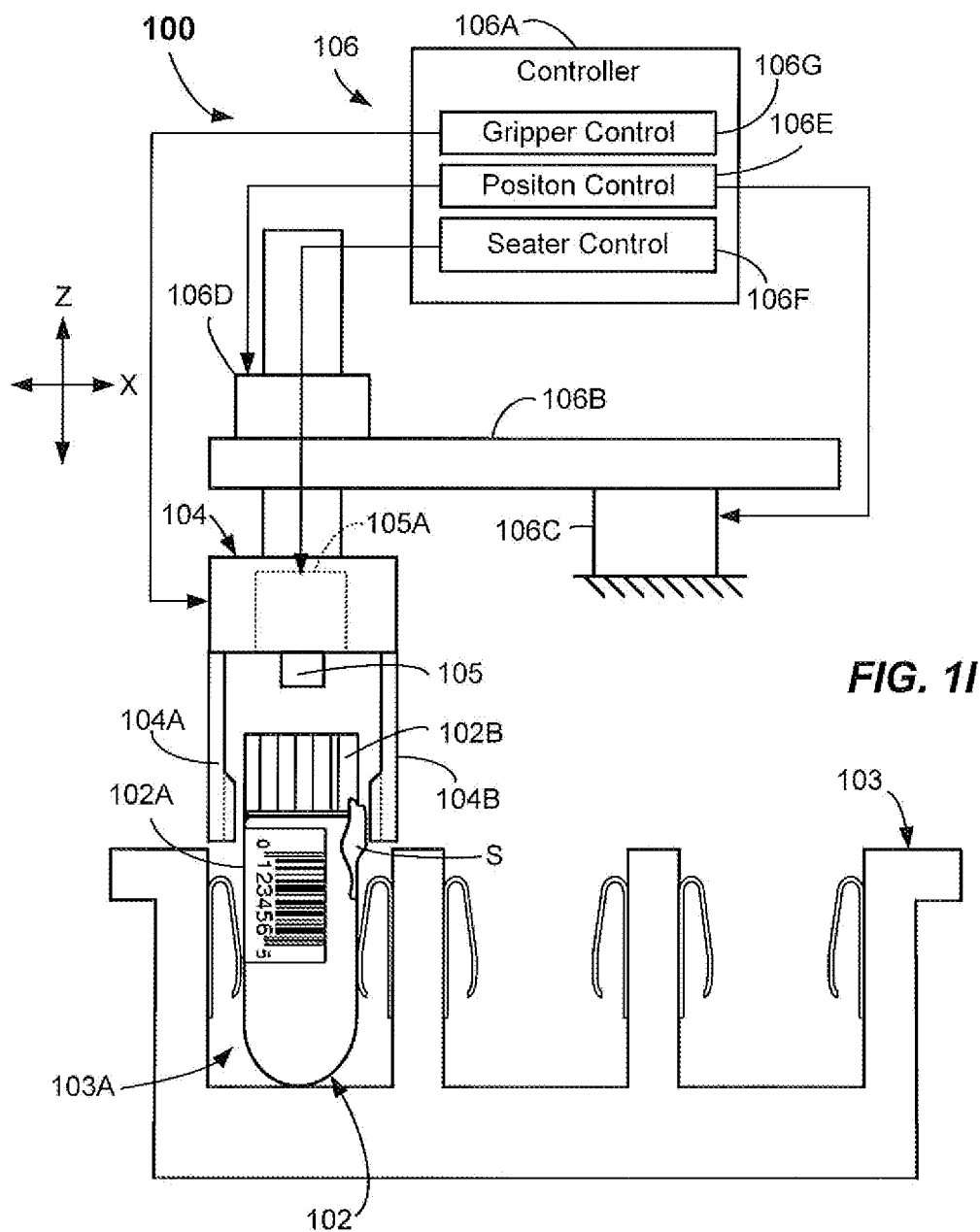
FIG. 1I is a side view of an example robotic system again decoupling the gripper fingers to the sample container and then further descending the gripper fingers to provide a shear force on any remaining adhesion between the sample container and gripper fingers according to embodiments of the invention.

Once the sample container 102 is inserted to the bottom 103B of the receptacle 103A, the gripper control 106G may again cause the gripper fingers 104A, 104B to grip the sample container 102 as shown in FIG. 1H. Following this, the seater control 106F may cause the seater 105 to retract from the cap 102B as shown in FIG. 1H. Finally, once the seater 105 is retracted from the cap 102B, the position control 106E may cause the gripper assembly 104 to again ungrip the sample container 102 and further descend, as shown in FIG. 1I. For example, the gripper assembly 104 may further descend from the previous position by a few millimeters. Descending further provides a shearing action to separate any remaining adherence between the gripper fingers 104A, 104B and any sticky surfaces S on the sample container 102. As should be apparent, the present method provides a method adapted to reduce occurrences of improper sample container positioning due to the presence of sticky surfaces on sample containers (e.g., sample tubes).

A method of positioning a sample container of the invention will now be further explained with reference to FIG. 2. The method of positioning a sample container 200 includes, in 202, gripping the sample container 102 with gripper fingers 104A, 104B of a gripper assembly 104. This initial gripping in 202 may occur at a pickup location 101. Next, the gripper assembly 104 and sample container 102 are descended to partially insert the sample container 102 into a destination receptacle 103A in 206. The destination receptacle 103A may be a sample rack 103 or other suitable receptacle. Once partially inserted, the gripper fingers 104A, 104B are ungripped from the sample container 102 in 206. While ungripped, the sample container 102 is pushed into the destination receptacle 103A with a seater 105 in 208. In the preferred case, the sample container 102 is pushed into the receptacle 103A until bottomed out. After pushing with the seater 105, the sample container 102 is re-gripped with the gripper fingers 104A, 104B in 210. While the sample container 102 is being gripped, the seater 105 is retracted in 212. For example, the seater 105 is retracted from the cap 102B. Once the seater 105 is retracted from contact with the top of the sample container 102, the gripper fingers 104A, 104B are again ungripped from the sample container 102 in 214. When the sample container 102 is ungripped, the gripper fingers 104A, 104B are further descended in 216. This applies a shearing force between the gripper fingers 104A, 104B and any still adhered sticky material S.

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus, or methods disclosed but, to the contrary, the intention is to cover all modifications, equivalents, and alternatives falling within the spirit and scope of the invention.

What is claimed is:

1. A method of positioning a sample container, comprising:
    gripping the sample container with gripper fingers of a gripper assembly;
    descending the gripper assembly and sample container to partially insert the sample container into a destination receptacle;
    ungripping the gripper fingers from the sample container;
    while ungripped, pushing the sample container into the destination receptacle with a seater;
    re-gripping the sample container with the gripper fingers;
    retracting the seater;
    again ungripping the gripper fingers from the sample container; and
    further descending the gripper fingers
    wherein the further descending provides a shearing action to separate any remaining adherence between the gripper fingers and a sticky surface on the sample container.

2. The method of positioning of claim 1, further comprising:
    providing the sample container at a pickup location;
        gripping the sample container with the gripper fingers of the gripper assembly at the pickup location; and
        moving the gripper assembly and sample container to a location above the destination receptacle.

3. The method of positioning of claim 2, further comprising measuring a location of a top of the sample container at the pickup location.

4. The method of positioning of claim 3, further comprising measuring a location of a top of the sample container at a location above the pickup location.

5. The method of positioning of claim 2, further comprising measuring a location of a top of the sample container while positioned in a pickup receptacle at the pickup location.

6. The method of positioning of claim 2, wherein providing a sample container at a pickup location includes grappling the sample container with a container straightening device.

7. The method of positioning of claim 2, wherein prior to moving the gripper assembly and sample container to the location above the destination receptacle, determining if a position of the sample container has slipped in the gripper fingers.

8. The method of positioning of claim 2, wherein after moving the gripper assembly and sample container to the location above the destination receptacle, determining if a position of the sample container has slipped in the gripper fingers.

9. The method of positioning of claim 1, wherein the sample container includes a sample container body and cap and a sticky surface is on the sample container body or cap.

10. The method of positioning of claim 1, wherein the pushing of the sample container into the destination receptacle with the seater causes the sample container to bottom out in the receptacle.

11. The method of positioning of claim 9, wherein the seater is locked during the pushing.

12. The method of positioning of claim 1, wherein the destination receptacle is in a sample rack.

\* \* \* \* \*